(12) United States Patent  
Momoda et al.

(10) Patent No.: US 6,525,194 B1
(45) Date of Patent: Feb. 25, 2003

(54) CHROMENE COMPOUND

(75) Inventors: Junji Momoda, Tokuyama (JP); Shingo Matsuoka, Tokuyama (JP); Hironobu Nagou, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/153,911

(22) Filed: May 24, 2002

Related U.S. Application Data

(63) Continuation of application No. 09/762,112, filed on Apr. 23, 2001, now abandoned.

(30) Foreign Application Priority Data

Jun. 3, 1999 (JP) .............................. 11-156270
Jul. 19, 1999 (JP) .............................. 11-205166
May 29, 2000 (JP) ................... PCT/JP00/03458

(51) Int. Cl.$^7$ .................. C07D 37/92; C07D 405/05
(52) U.S. Cl. .................. 544/90; 544/43; 544/129; 544/142; 549/389
(58) Field of Search ................ 544/111, 143, 544/129, 142; 549/389

(56) References Cited

U.S. PATENT DOCUMENTS 6,022,496 A * 2/2000 Kawabata et al.
6,291,561 B1 * 9/2001 Breyne et al. ................. 524/96
6,294,112 B1 * 9/2001 Clarke et al. ................ 252/586

FOREIGN PATENT DOCUMENTS

| JP | 11322739 | * 11/1999 |
| WO | WO 94/22850 | * 10/1994 |
| WO | WO 98/45281 | * 10/1998 |
| WO | WO 99/31081 | * 6/1999 |

* cited by examiner

Primary Examiner—Joseph K. McKane
Assistant Examiner—Andrea D. Small
(74) Attorney, Agent, or Firm—Sherman & Shalloway

(57) ABSTRACT

A chromene compound which develops yellow to red color, a high color density and a little initial color and which, when used in combination with an existing photochromic compound that exhibits blue color so as to develop a neutral tint, maintains uniformity in the color tone at the time of developing color or fading color, or exhibits a very large color fading rate. The chromene compound has a naphthopyran cyclic skeleton, and is expressed by, for example, the following formula in which a substituent such as substituted amino group or morpholino group is bonded to the sixth position of the naphthopyran ring through a nitrogen atom, and two aryl groups having a particular substituent are bonded to the third position thereof,

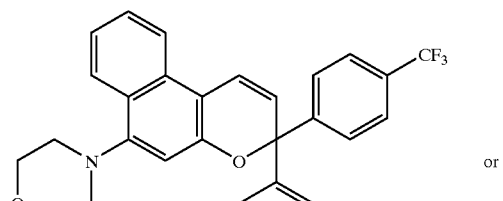

or 3 Claims, 2 Drawing Sheets

CHROMENE COMPOUND

CROSS REFERENCE TO RELATED APPLICATION

This application is a continuation of application Ser. No. 09/762,112, filed on Apr. 23, 2001, now abandoned, which claims priority from PCT application PCT/JP00/03458 filed May 29, 2000, published in Japanese on Dec. 14, 2000, which in turn claims priority from Japanese Patent Application 156270/99 filed Jun. 03, 1999 and 205166/99 filed Jul. 19, 1999.

TECHNICAL FIELD

The present invention relates to a chromene compound which changes into a state of being colored in a yellowish to reddish color tone upon the irradiation with light containing ultraviolet rays such as of sunlight or light from a mercury lamp, the change being reversible, the color being quickly developed, the color density being high, and exhibiting little color when it is not developing color.

BACKGROUND ART

Photochromism is a phenomenon that is drawing attention in these several years, and is a reversible action of a compound which quickly changes its color when it is irradiated with light containing ultraviolet rays such as sunlight or light of a fluorescent lamp and resumes its initial color when it is no longer irradiated with light but is placed in a dark place. The compound having this property is called photochromic compound. Various compounds have so far been synthesized and have been used in a variety of fields.

When the photochromic compound is used as an optical material such as photochromic lenses for spectacles, a simple change in the color upon the irradiation with light or upon discontinuation of irradiation with light, is not enough. That is, a variety of properties are required, such as the material remains transparent (i.e., the photochromic compound has no initial color) in a state of not being irradiated with light, the material quickly develops color when it is irradiated with light in a desired color tone maintaining a sufficient degree of density, the color quickly fades away when the material is no longer irradiated with light, and the above properties are not deteriorated even after the material is used for extended periods of time (i.e., the material has a high durability).

In the field of photochromic spectacle lenses, in particular, a color tone that greatly affects the liking of the users serves as a very important factor, and it has been desired to maintain a neutral tint such as grey or brown which is considered to be the most desired color tone of lenses in this field of use not only when the color has been developed but also in a step of developing color and in a step in which the color fades away.

Many photochromic compounds have heretofore been proposed for photochromic lenses for spectacles, but no compound that satisfies the above requirements has been known yet.

As for the color tone, for example, it is difficult to obtain the above neutral tint relying upon one kind of photochromic compound only. Usually, the neutral tint is obtained by mixing a photochromic compound that develops yellowish to reddish color (hereinafter also referred to as yellow to red compound) and a photochromic compound that develops blue color (hereinafter also referred to as blue compound). Due to different color developing/fading rates between the two compounds, however, there occurs such a problem that the color tone becomes nonuniform at the time when the color is being developed or faded away.

That is, as the yellow to red compound, there has been known a chromene compound and as the blue compound, there has been known a spirooxazine-type compound or a fulgimide-type compound. In general, human eyes are more sensitive to blue than yellow or red. To obtain the above-mentioned uniform color tone, therefore, it is desired that the yellow to red compound develops color faster than the blue compound and, conversely, fades moderately slower than bule compound. The blue compound develops color at a relatively high rate, and there arises no problem when the color-developing rate of the yellow to red compound is comparable thereto. However, very few blue compounds that exhibit a high fading rate have been known. When the yellow to red compound having a high fading rate is used, therefore, the color tone becomes nonuniform at the time when the color fades away.

For example, PCT International Laid-Open Specification WO98/45281 discloses a chromene compound of the following formula (A) that develops orange color.

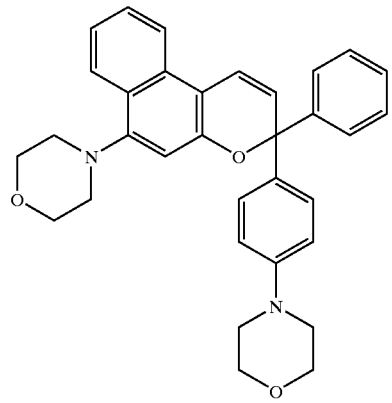

(A)

This chromene compound, however, has both a low color developing rate and a low color fading rate. When used in combination with a known blue compound to obtain a composition that exhibits a neutral tint, therefore, this compound arouses a problem in that the color tone in the fading step becomes blue.

Japanese Unexamined Patent Publication (Kokai) No. 298176/1998 discloses a compound represented by the following formula (B),

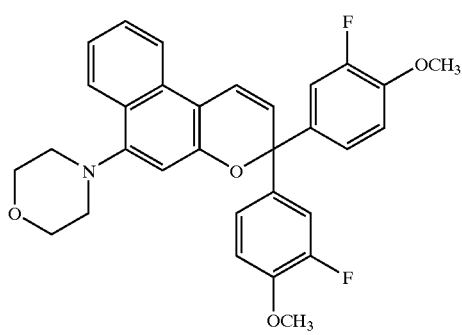

(B)

The color fading rate of this compound is lower than that of the above compound (A) but is not still satisfactory.

Further, U.S. Pat. No. 4,980,089 discloses a chromene compound represented by the following formula (C),

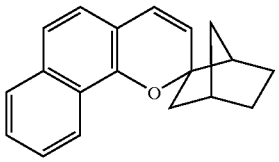

(C)

Contrary to the above-mentioned two kinds of chromene compounds, however, this compound exhibits a too low color developing rate and a too low color fading rate, making it quite difficult to obtain uniformity in the step of developing color and in the step of fading color.

When it is attempted to obtain a neutral tint such as grey or brown by using the known chromene compound that develops yellow to red color in combination with the blue compound that has heretofore been used as described above, the color tone is not uniform in the step of developing color or in the step of fading color, and is not still satisfactory.

Besides, the photochromic compounds known thus far are not necessarily satisfactory with respect to the fading rate and the initial color.

For example, the chromene compound represented by the above general formula (A) disclosed in the above PCT International Laid-Open Specification WO98/45281 exhibits a relatively high fading rate but has a large initial color which casts a problem.

The chromene compound represented by the above general formula (B) disclosed in the above Japanese Unexamined Patent Publication (Kokai) No. 298176/1998 exhibits a relatively high fading rate and an improved initial color. The fading rate, however, is not still satisfactory when the chromene compound is used alone or when it is considered that the chromene compound will be used in combination with a blue compound having a very high fading rate that may be developed in the future.

DISCLOSURE OF THE INVENTION

It is therefore an object of the present invention to provide a novel chromene compound which exhibits at least one of the above-mentioned properties that are required when it is used for such applications as photochromic lenses for spectacles, the property being superior to that of the conventional photochromic compounds and, particularly, that of the conventional chromene compounds.

More concretely, the object of the present invention is to provide a chromene compound which has a high color density and a little initial color and which, when used in combination with a blue compound that is now being used, provides a uniform color tone in the steps of developing and fading color or, in other words, which exhibits nearly the same color developing rate as that of the blue compound that is now being used, exhibits a color fading rate which is low to a suitable degree, or exhibits a very high color fading rate.

In order to accomplish the above object, the present inventors have conducted keen study concerning the effect of when various substituents are introduced into the chromene compound. As a result, the present inventors have found the fact that the novel chromene compounds having a naphthopyran skeleton, particular substituents at the third and sixth positions of the naphthopyran ring and, as required, particular substituents at the seventh to tenth positions, exhibit a common feature in that a little initial color and a high color density exhibit a high color developing rate and a suitably low color fading rate depending upon the kind of the substituent, do not cause the color tone to lose balance at the step of fading when the compound is used being mixed together with the conventional blue compound, or exhibit a very high color fading rate, and have thus arrived at the present invention.

That is, the present invention is concerned with a chromene compound represented by the following general formula (1),

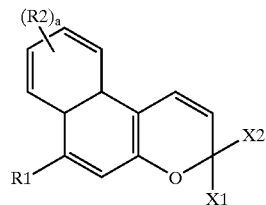

(1)

wherein

R1 is a substituted amino-group, a substituted or unsubstituted heterocyclic group having a nitrogen atom, as a hetero atom, bonded to a naphthopyran ring through the nitrogen atom, or a condensed heterocyclic group in which said heterocyclic group is condensed with an aromatic hydrocarbon ring or an aromatic heterocyclic ring, R2 is an alkyl group, an alkoxyl group, an aralkoxyl group, an aralkyl group, a substituted amino group, a cyano group, a substituted or unsubstituted aryl group, a halogen atom, a substituted or unsubstituted heterocyclic group having, as a hetero atom, a nitrogen atom, bonded to the naphthopyran ring through the nitrogen atom, or a condensed heterocyclic group in which said heterocyclic group is condensed with an aromatic hydrocarbon ring or an aromatic heterocyclic ring, "a" representing the number of the substituents R2 is an integer of 0 to 3, X1 is a group represented by the following formula (2),

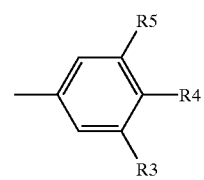

(2)

wherein each of R3, R4 and R5 is a hydrogen atom, a substituted amino group, a substituted or unsubstituted heterocyclic groups, having a nitrogen atom, as a hetero atom, bonded to the benzene ring, or a condensed heterocyclic group in which said heterocyclic group is condensed with an aromatic hydrocarbon ring or an aromatic heterocyclic ring, but R3, R4 and R5 are not hydrogen atoms simultaneously, and X2 is a group represented by the following formula (3),

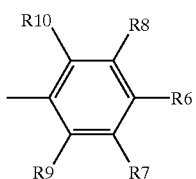
(3)

wherein
R6 is a hydrogen atom; an electron attractive group selected from the group consisting of a trifluoromethyl group, a trifluoromethoxy group, a cyano group, a sulfonyl group, an alkylsulfonyl group, an arylsulfonyl group and a nitro group; or an alkoxyl group,
each of R7 and R8 is (i) a hydrogen atom, an aliphatic hydrocarbon group having not less than three carbon atoms, a halogen atom, a trifluoromethyl group, a trifluoromethoxy group, a cyano group, a sulfonyl group, an alkylsulfonyl group, an arylsulfonyl group or a nitro group when R6 is not a hydrogen atom, or (ii) a hydrogen atom, a halogen atom, a trifluoromethyl group or a trifluoromethoxy group when R6 is a hydrogen atom,
each of R9 and R10 is a hydrogen atom, a cyano group, an alkoxyl group having 1 to 5 carbon atoms, a fluorine atom or a chlorine atom,
wherein, when R4 in the group represented by the above formula (2) is the substituted amino group, the substituted or unsubstituted heterocyclic group having or condensed heterocyclic group, R6 is not an alkoxyl group, and R6, R7, R8, R9 and R10 are not hydrogen atoms simultaneously.

The above chromene compound has a feature of little initial color and a high density of color that is developed.

Among the chromene compounds of the present invention represented by the above general formula (1), the chromene compound in which:
R6, R7, R8, R9 and R10 in the above formula (3) are not hydrogen atoms simultaneously,
R6 is a hydrogen atom or an electron attractive group selected from the group consisting of a trifluoromethyl group, a cyano group, a sulfonyl group, an alkylsulfonyl group, an arylsulfonyl group and a nitro group,
when R6 is not a hydrogen atom, each of R7 and R8 is a hydrogen atom, an aliphatic hydrocarbon group having not less than 3 carbon atoms, a fluorine atom, a trifluoromethyl group, a cyano group, a sulfonyl group, an alkylsulfonyl group, an arylsulfonyl group or a nitro group, and
when R6 is a hydrogen atoms, each of R7 and R8 is a hydrogen atom,
exhibits a high color developing rate and a suitably low color fading rate in addition to the feature of little initial color and a high density of color that is developed, and does not cause the color tone to lose balance in the step of fading when it is used being mixed together with the conventional blue compound.

Among the chromene compounds of the present invention represented by the above general formula (1), further, the chromene compound in which:
R6 in the above formula (3) is a hydrogen atom, an alkoxyl group or a trifluoromethoxy group,
each of R7 and R8 is a hydrogen atom, a halogen atom, a trifluoromethyl group or a trifluoromethoxy group [wherein both R7 and R8 are not hydrogen atoms, when R4 in the formula (2) in the general formula (1) is the substituted amino group, the substituted or unsubstituted heterocyclic group or the condensed heterocyclic group], and
both R9 and R10 are hydrogen atoms,
has a feature of a high fading rate in addition to the feature of little initial color and a high density of color that is developed.

Another invention is concerned with a photochromic material containing the chromene compound of the present invention, and a further invention is concerned with a photochromic optical material containing the chromene compound of the present invention.

According to the present invention, further, there is provided a photochromic polymerizable composition containing the above-mentioned chromene compound, a polymerizable monomer (particularly, a (meth)acrylic acid ester compound) and, as required, a polymerization initiator.

BEST MODE FOR CARRYING OUT THE INVENTION

[Chromene Compound]

Figure 1:
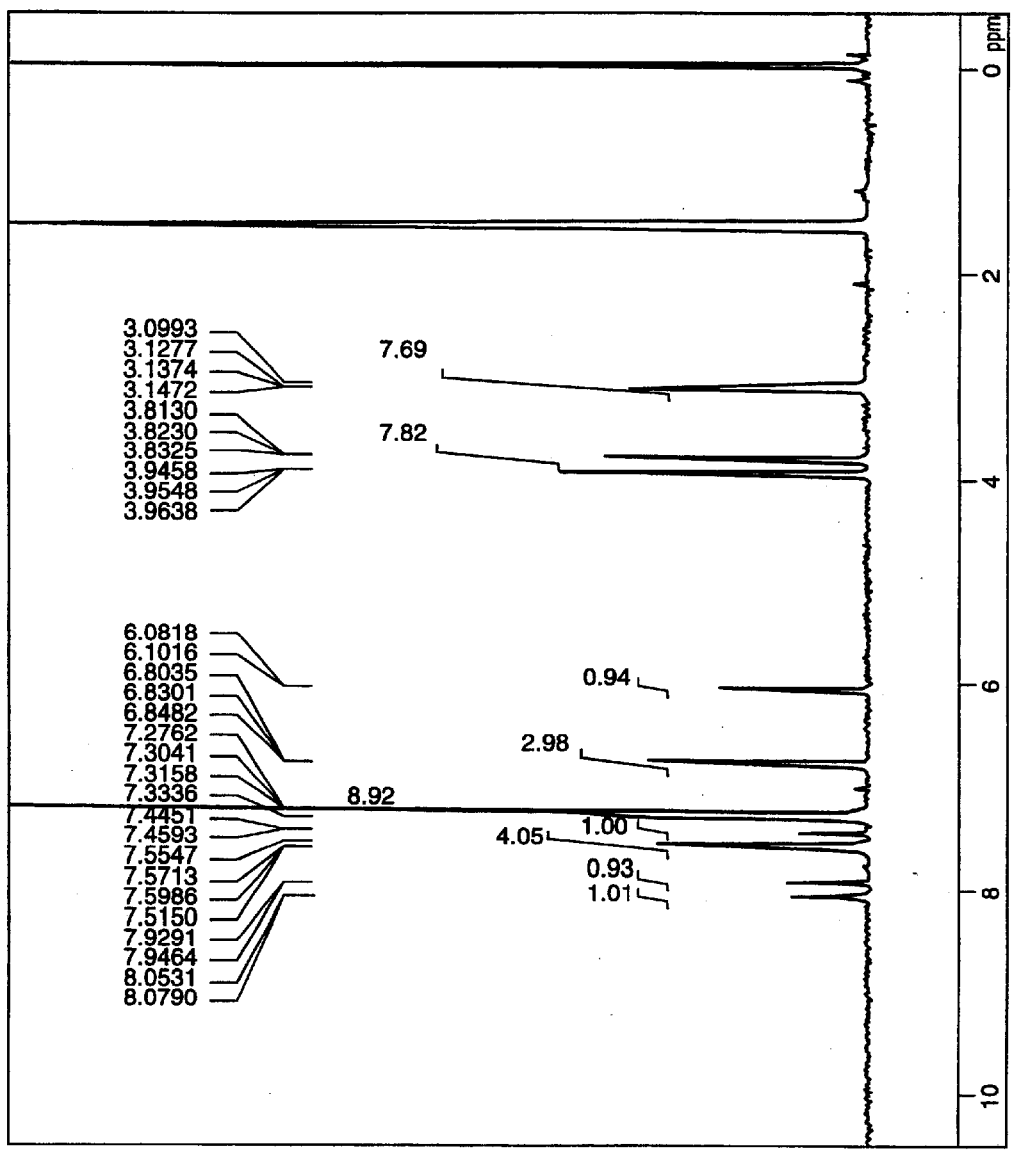
FIG. 1 shows proton nuclear magnetic resonance spectra of a compound of Example 1.

A. In the above general formula (1), the substituent R1 bonded to the sixth position of the naphthopyran ring is (A-1) a substituted amino group, (A-2) a substituted or unsubstituted heterocyclic group having a nitrogen atom as a hetero atom and is bonded to the naphthopyran ring through the nitrogen atom, or (A-3) a condensed heterocyclic group in which the heterocyclic group is condensed with an aromatic hydrocarbon ring or an aromatic heterocyclic ring. In the above substituted or unsubstituted heterocyclic group, the words "having a nitrogen atom as a hetero atom and is bonded to the naphthopyran ring through the nitrogen atom" have a meaning in that, when "—" of —R1 is called unbonded hand, the unbonded hand exists in the nitrogen atom that is included as a hetero atom, and the nitrogen atom is bonded to the naphthopyran ring.

As the substituted amino group (A-1), though there is no particular limitation, there can be preferably exemplified alkylamino group, dialkylamino group, arylamino group or diarylamino group substituted with alkyl group or aryl group and, particularly, with alkyl group having 1 to 4 carbon atoms or aryl group having 6 to 10 carbon atoms. Preferred examples of the substituted amino group include methylamino group, ethylamino group, phenylamino group, dimethylamino group, diethylamino group and diphenylamino group.

There is no particular limitation on the substituted or unsubstituted heterocyclic group (A-2) having a nitrogen atom as a hetero atom and is bonded to the naphthopyran ring through the nitrogen atom, or on the condensed heterocyclic group (A-3) in which the heterocyclic group is condensed with an aromatic hydrocarbon ring or a aromatic heterocyclic ring. It is, however, preferred that the number of carbon atoms constituting the heterocyclic group is from 2 to 10 and, particularly, from 2 to 6. Further, the rings of these groups may contain a hetero atom other than the nitrogen atom bonded to the naphthopyran ring. Though there is no particular limitation, the hetero atom may be an oxygen atom, a sulfur atom or a nitrogen atom.

As the substituent in the case when the heterocyclic group has the substituent, there can be exemplified an alkyl group and, particularly, an alkyl group having 1 to 4 carbon atoms; an alkoxyl group and, particularly, an alkoxyl group having 1 to 5 carbon atoms; a substituted amino group and, particularly, a substituted amino group substituted with an alkyl group having 1 to 4 carbon atoms and/or an aryl group having 6 to 10 carbon atoms; and an aryl group and, particularly, an aryl group having 6 to 10 carbon atoms. In this case, the substituent may be bonded to the carbon atom or may be bonded to the other hetero atom, and there is no particular limitation on the number of the substituents. Preferably, however, the number of the substituents is 1 or 2.

Preferred examples of the group (A-2) or (A-3) include morpholino group, piperidino group, pyrrolidinyl group, piperazino group, N-methylpiperazino group and indolinyl group.

B. In the above general formula (1), R2 is (B-1) an alkyl group, (B-2) an alkoxyl group, (B-3) an aralkoxyl group, (B-4) an aralkyl group, (B-5) a substituted amino group, (B-6) a cyano group, (B-7) a substituted or unsubstituted aryl group, (B-8) a halogen atom, (B-9) a substituted or unsubstituted heterocyclic group having a nitrogen atom as a hetero atom and is bonded to the naphthopyran ring through the nitrogen atom, or (B-10) a condensed heterocyclic group in which the heterocyclic group is condensed with an aromatic hydrocarbon ring or an aromatic heterocyclic ring. Described below are the substituents represented by R2 except the cyano group (B-6) of which the structure has been known.

Though there is no particular limitation, the alkyl group (B-1) usually has 1 to 4 carbon atoms. Preferred examples of the alkyl group include methyl group, ethyl group, n-propyl group, isopropyl group, n-butyl group, sec-butyl group and t-butyl group.

Though there is no particular limitation, the alkoxyl group (B-2) usually has 1 to 5 carbon atoms. Preferred examples of the alkoxyl group include methoxy group, ethoxy group, n-propoxy group, isopropoxy group, n-butoxy group, sec-butoxy group and t-butoxy group.

Though there is no particular limitation, the aralkoxyl group (B-3) preferably has 6 to 10 carbon atoms. Preferred examples of the aralkoxyl group include phenoxy group and naphthoxy group.

Though there is no particular limitation, it is desired that the aralkyl group (B-4) has 7 to 11 carbon atoms. Preferred examples of the aralkyl group include benzyl group, phenylethyl group, phenylpropyl group and phenylbutyl group.

The substituted amino group (B-5) is the same as that of (A-1) represented by R1.

Though there is no particular limitation, the substituted or unsubstituted aryl group (B-7) is preferably an unsubstituted aryl group having 6 to 10 carbon atoms. Preferred examples of the unsubstituted aryl group include phenyl group and naphthyl group.

As the substituted aryl group, there can be exemplified the one in which one or two or more hydrogen atoms of the unsubstituted aryl group are substituted with substituents. As the substituent, there can be exemplified alkyl group, alkoxyl group, substituted amino group, aryl group, substituted or unsubstituted heterocyclic group having a nitrogen atom as a hetero atom and is bonded to the aryl group through the nitrogen atom, and a condensed heterocyclic group in which the heterocyclic group is condensed with an aromatic hydrocarbon ring or an aromatic heterocyclic ring. Here, the alkyl group, alkoxyl group, substituted amino group and aryl group are the same as those (B-1), (B-2), (B-5) and unsubstituted aryl group described above. The substituted or unsubstituted heterocyclic group and condensed heterocyclic group are the same as the "substituted or unsubstituted heterocyclic group having a nitrogen atom as a hetero atom and is bonded to the naphthopyran ring through the nitrogen atom" of (A-2) represented by R1 and the "condensed heterocyclic group in which the heterocyclic group is condensed with an aromatic hydrocarbon ring or an aromatic heterocyclic ring" of (A-3), except that the ring bonded through the nitrogen atom is changed from the naphthopyran ring into an aromatic ring of the aryl group.

As the halogen atom (B-8), there can be exemplified a fluorine atom, a chlorine atom, a bromine atom or an iodine atom.

The substituted or unsubstituted heterocyclic group (B-9) having a nitrogen atom as a hetero atom and is bonded to the naphthopyran ring through the nitrogen atom or the condensed heterocyclic group (B-10) in which the heterocyclic group is condensed with an aromatic hydrocarbon ring or an aromatic heterocyclic ring, is the same as those of (A-2) and (A-3) represented by R1.

"a" representing the number of the substituents R2 is an integer of 0 to 3. When "a" is 2 or 3, the substituents R2 may be different from each other. There is no particular limitation on the position onto where the substituents are bonded provided the position is the seventh position, eighth position, ninth position or tenth position of the naphthopyran ring, and there is no particular limitation on the total number thereof either. Preferably, however, the total number of the substituents present on these positions is not larger than 2.

C. In the above general formula (1), a substituent X1 which is one of the substituents bonded to the third position of the naphthopyran ring is represented by the following formula (2),

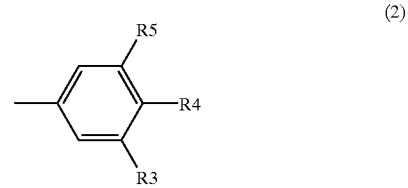

(2)

wherein each of R3, R4 and R5 is (C-1) a hydrogen atom, (C-2) a substituted amino group, (C-3) a substituted or unsubstituted heterocyclic group having a nitrogen atom, as a hetero atom, bonded to the benzen ring, or (C-4) a condensed heterocyclic group in which a heterocyclic group is condensed with an aromatic hydrocarbon ring or an aromatic heterocyclic ring, but wherein R3, R4 and R5 are not hydrogen atoms simultaneously.

When these groups are hydrogen atoms simultaneously, the fading rate becomes very small, and the effect of the invention is not obtained.

Here, the substituted amino group (C-2) is the same as the substituted amino group (A-1) represented by R1. Further, the groups (C-3) and (C-4) are the same as those of (A-2) and (A-3) represented by R1 except that the ring to which the nitrogen atom is bonded is changed from the naphthopyran ring into the benzene ring.

D. Another substituent X2 bonded to the third position of the naphthopyran ring in the above general formula (1) is represented by the following formula (3),

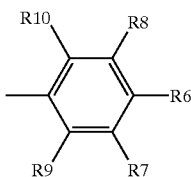

(3)

wherein R6 is (D-1) a hydrogen atom; an electron attractive group selected from the group consisting of (D-2) a trifluoromethyl group, (D-3) a trifluoromethoxy group, (D-4) a cyano group, (D-5) a sulfonyl group, (D-6) an alkylsulfonyl group, (D-7) an arylsulfonyl group and (D-8) a nitro group; or (D-9) an alkoxyl group.

Here, however, R6 is not the alkoxyl group (D-9) when R4 in the group represented by the above formula (2) is the substituted amino group (C-2), the substituted or unsubstituted heterocyclic group having a nitrogen atom as a hetero atom and is bonded to the benzene ring through the nitrogen atom (C-3), or the condensed heterocyclic group in which the heterocyclic group is condensed with an aromatic hydrocarbon ring or an aromatic heterocyclic ring (D-4). When R4 is the above group and R6 is the alkoxyl group, the initial color becomes so conspicuous that the effect of the invention is not obtained.

Described below are (D-6) the alkylsulfonyl group and (D-7) the arylsulfonyl group represented by R6, which may have plural structures. Though there is no particular limitation, it is desired that (D-6) the alkylsulfonyl group is the one having 1 to 4 carbon atoms, such as methylsulfonyl group, ethylsulfonyl group, propylsulfonyl group or t-butylsulfonyl group. Further, though there is no particular limitation, it is desired that (D-7) the arylsulfonyl group is the one having 6 to 10 carbon atoms, such as phenylsulfonyl group or naphthylsulfonyl group.

E. In the above formula (3), further, R7 and R8 have structures that differ depending upon R6. That is, (i) when R6 is not the hydrogen atom (D-1), each of R7 and R8 is a hydrogen atom (E-1), an aliphatic hydrocarbon group having not less than three carbon atoms (E-2), a halogen atom (E-3), a trifluoromethyl group (E-4), a trifluoromethoxy group (E-5), a cyano group (E-6), a sulfonyl group (E-7), an alkylsulfonyl group (E-8), an arylsulfonyl group (E-9) or a nitro group (E-10). Or, (ii) when R6 is a hydrogen atom, each of R7 and R8 is a hydrogen atom (E-1), a halogen atom (E-3), a trifluoromethyl group (E-4) or a trifluoromethoxy group (E-5). When the above conditions (i) and (ii) are not satisfied, there is obtained neither the effect of a large color developing rate and a suitably small color fading rate nor the effect of a large color fading rate and little initial color.

Here, though there is no particular limitation, (E-2) the aliphatic hydrocarbon group having not less than 3 carbon atoms is preferably an alkyl group having not less than 3 carbon atoms and, particularly, having 3 to 6 carbon atoms, such as n-propyl group, isopropyl group, n-butyl group or t-butyl group; or a cycloalkyl group having not less than 3 carbon atoms and, particularly, 3 to 8 carbon atoms, such as cyclopropyl group, cyclohexyl group, adamantilydene group or norbornilydene group. When the aliphatic hydrocarbon group has not more than 3 carbon atoms, a suitably low color fading rate, which is one of the effects of the invention, is not obtained.

As the halogen atom (E-3), there can be exemplified a fluorine atom, a chlorine atom, a bromine atom or an iodine atom.

The alkylsulfonyl group (E-8) and the arylsulfonyl group (E-9) are the same as those (D-6) and (D-7) represented by R6.

F. In the above formula (3), each of R9 and R10 is (F-1) a hydrogen atom, (F-2) a cyano group, (F-3) an alkoxyl group having 1 to 5 carbon atoms, (F-4) a fluorine atom or (F-5) chlorine atom.

Among the chromene compounds of the present invention, a chromene compound which is preferred from the standpoint of effects and easy synthesis is the one in which:

each of the group (A-1), (B-5) and (C-2) is a substituted amino group having an alkyl group with 1 to 4 carbon atoms and/or an aryl group with 6 to 10 carbon atoms {these groups (A-1), (B-5) and (C-2) are hereinafter expressed as (A'-1), (B'-5) and (C'-2) respectively};

each of the group (A-2), (B-9) and (C-4) is a substituted or unsubstituted heterocyclic group having a nitrogen atom as a hetero atom and is bonded to the naphthopyran ring through the nitrogen atom, the number of the carbon atoms constituting the heterocyclic group being from 2 to 10 and, particularly, from 2 to 6 {here, the substituent is at least the one selected from alkyl group having 1 to 4 carbon atoms, alkoxyl group having 1 to 5 carbon atoms, substituted amino group (in which the substituent is an alkyl group having 1 to 4 carbon atoms and/or an aryl group having 6 to 10 carbon atoms), and an aryl group having 6 to 10 carbon atoms} {these groups (A-2), (B-9) and (C-4) are hereinafter expressed as (A'-2), (B'-9) and (C'-4) respectively};

each of the group (A-3), (B-10) and (C-5) is a condensed heterocyclic group in which the heterocyclic group is condensed with an aromatic hydrocarbon ring or an aromatic heterocyclic ring {these groups (A-3), (B-10) and (C-5) are hereinafter expressed as (A'-3), (B'-10) and (C'-5) respectively};

the group (B-1) is an alkyl group having 1 to 4 carbon atoms {this group (B-1) is hereinafter expressed as (B'-1)};

each of the group (B-2) and (D-9) is an alkoxyl group having 1 to 5 carbon atoms {these groups (B-2) and (D-9) are hereinafter expressed as (B'-2) and (D'-9) respectively};

the group (B-3) is an aralkoxyl group having 6 to 10 carbon atoms {this group (B-3) is hereinafter expressed as (B'-3)};

the group (B-4) is an aralkyl group having 7 to 11 carbon atoms {this group (B-4) is hereinafter expressed as (B'-4)};

the group (B-7) is a substituted or unsubstituted aryl group having 6 to 10 carbon atoms (without including the carbon atoms of the substituent) {here, the substituent is at least the one selected from an alkyl group having 1 to 4 carbon atoms, an alkoxyl group having 1 to 5 carbon atoms, a substituted amino group (where the substituent is an alkyl group having 1 to 4 carbon atoms and/or an aryl group having 6 to 10 carbon atoms), an aryl group having 6 to 10 carbon atoms, a heterocyclic group having a nitrogen atom as a hetero atom and is substituted or is not substituted with the aryl group through the nitrogen atom (where the substituent is at least the one selected from an alkyl group having 1 to 4 carbon atoms, an alkoxyl group having 1 to 5 carbon atoms, a substituted amino group substituted within alkyl group having 1 to 4 carbon atoms and/or an aryl group having 6 to 10 carbon atoms, and an aryl group having 6 to 12 carbon atoms), and a condensed heterocyclic group in which the heterocyclic group is condensed with an aromatic hydrocarbon ring or an aromatic heterocyclic ring} {this group (B-7) is hereinafter expressed as (B'-7)};

each of the group (D-6) and (E-8) is an alkylsulfonyl group having 1 to 4 carbon atoms {these groups (D-6) and (E-8) are hereinafter expressed as (D'-6) and (E'-8) respectively};

each of the group (D-7) and (E-9) is an arylsulfonyl group having 6 to 10 carbon atoms {these groups (D-7) and (E-9) are hereinafter expressed as (D'-7) and (E'-9) respectively}; and the group (E-2) is an alkyl group having 3 to 6 carbon atoms or a cycloalkyl group having 3 to 8 carbon atoms {this group (E-2) is hereinafter expressed as (E'-2)}.

The chromene compounds of the present invention exhibit a common effect of a high density of color that is developed and little initial color. Depending upon the combinations of various substituents represented by the above formula (3), however, there are obtained different additional effects.

That is, a chromene compound (hereinafter simply referred to as the chromene compound 2) in which:

R6, R7, R8, R9 and R10 in the formula (3) are not hydrogen atoms simultaneously, R6 is a hydrogen atom, or is an electron attractive group selected from the group consisting of a trifluoromethyl group, a cyano group, a sulfonyl group, an alkylsulfonyl group, an arylsulfonyl group and a nitro group, when R6 is not the hydrogen atom, each of R7 and R8 is a hydrogen atom, an aliphatic hydrocarbon group having not less than 3 carbon atoms, a fluorine atom, a trifuloromethyl group, a cyano group, a sulfonyl group, an alkylsulfonyl group, an arylsulfonyl group or a nitro group, and when R6 is the hydrogen atom, both R7 and R8 are hydrogen atoms, exhibits a high color developing rate, a suitably low color fading rate, and does not cause the color tone to lose balance in the step of fading when it is used being mixed with the conventional blue compound.

As the conventional blue compound, there can be used any known blue photochromic compound without any particular limitation. There can be used, for example, a spirooxazine, a fulgimide and a blue (i.e., a maximum absorption wavelength of 550 to 620 nm) chromene compound taught in U.S. Pat. No. 4,913,544, EP 0600669, U.S. Pat. Nos. 4,882,438 and 5,708,063 and DE 19902771. The blue compounds taught in these literatures have fading rates two to four times as large as the fading rate of the chromene compound 2, and maintain a well-balanced color tone in the step of fading by taking into consideration a difference in the sensitivities of human eyes to yellow to red color developed by the chromene compound 2 of the present invention and to violet to blue color developed by the compounds disclosed in the literatures.

Among the chromene compounds of the present invention represented by the above general formula (1), further, the chromene compound (hereinafter simply referred to as the chromene compound 3) in which:

the group R6 in the formula (3) in the general formula (1) is a hydrogen atom, an alkoxyl group or a trifluoromethoxy group, each of R7 and R8 is a hydrogen atom, a halogen atom, a trifluoromethyl group or a trifluoromethoxy group {where R7 and R8 are not both hydrogen atoms when R4 in the formula (2) in the general formula (1) is a substituted amino group, a substituted or unsubstituted heterocyclic group having a nitrogen atom as a hetero atom and is bonded to the benzene ring through the nitrogen atom, or a condensed heterocyclic group in which the heterocyclic group is condensed with an aromatic hydrocarbon ring or an aromatic heterocyclic ring}, and both R9 and R10 are hydrogen atoms, exhibits a high color fading rate.

As concerns the chromene compound 2, it is desired that in the above formula (3);

① R6 is not the hydrogen atom, and R7, R8, R9 and R10 are all hydrogen atoms;

② R9 (or R10) is not the hydrogen atom, and R6, R7, R8 and R10 (or R9) are all hydrogen atoms;

③ R6 and R7 (or R8) are not hydrogen atoms, and R8 (or R7), R9 and R10 are hydrogen atoms;

④ R6 and R9 (or R10) are not hydrogen atoms, and R7, R8 and R10 (or R9) are hydrogen atoms; or ⑤ R6, R7 and R8 are not hydrogen atoms, and R9 and R10 are hydrogen atoms. When used being mixed with the conventional blue compound, such the chromene compound 2 exhibits a suitable degree of color fading rate maintaining a particularly good balance in the color tone in the step of fading, and can, further, be easily synthesized.

Among the chromene compounds 2, a chromene compound represented by the following formula (4) is particularly preferred from the standpoint of effect,

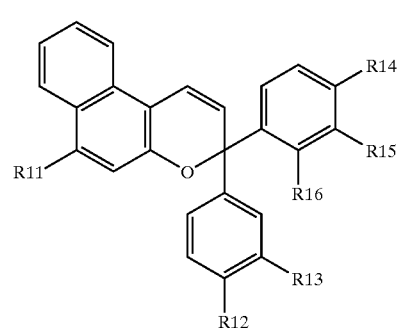

(4)

wherein

R11 is (A'-1), (A'-2) or (A'-3),

R12 and R13 are, respectively, (C-1), (C'-2), (C'-3) or (C'-4), and R12 and R13 are not (C-1) simultaneously, R14 is (D-1), (D-2), (D-4), (D-5), (D'-6), (D'-7) or (D-8), R15 is (E-1), R16 is (F-1), (F-2), (F-3), (F-4) or (F-5), and two of R14, R15 and R16 are hydrogen atoms.

Concrete examples of the chromene compound 2 include 6-morpholino-3-(4'-morpholinophenyl)-3-(4'-trifluorophenyl)-3H-benzo(f)chromene; 6-morpholino-3-(3'-morpholinophenyl)-3-(2'-fluorophenyl)-3H-benzo(f)chromene; 6-indolino-3-(4'-morpholinophenyl)-3-4'-cyanophenyl)-3H-benzo(f)chromene, etc.

Among the chromene compounds 3, further, a chromene compound represented by the following formula (5) is particularly preferred from the standpoint of effect,

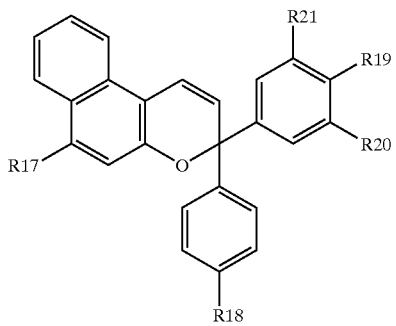

(5)

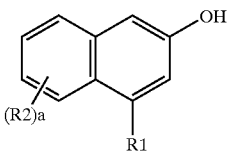

(6)

wherein R1, R2 and "a" are as defined in the above general formula (1),
and a propargyl alcohol derivative represented by the following general formula (7),

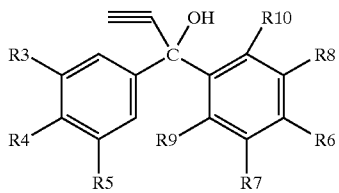

(7)

wherein

R17 is (A'-1), (A'-2) or (A'-3),

R18 is (C'-2), (C'-3) or (C'-4),

R19 is (D-1) or (D-3), and each of R20 and R21 is, independently from each other, (E-1), a fluorine atom or (E-4).

Concrete examples of the chromene compound 3 include 6-morpholino-3-(4'-morpholinophenyl)-3-(3'-fluorophenyl)-3H-benzo(f)chromene; 6-morpholino-3-(4'-morpholinophenyl)-3-(3'-trifluoromethylphenyl)-3H-benzo(f)chromene; 6-morpholino-3-(4'-morpholinophenyl)-3-(4'-trifluoromethoxyphenyl)-3H-benzo(f)chromene; 6-indolino-3-(3'-morpholinophenyl)-3-phenyl-3H-benzo(f)chromene; 6-morpholino-3-(4'-piperidinophenyl)-3-(3',5'-difluorophenyl)-3H-benzo(f)chromene, etc.

The chromene compound represented by the above general formula (1) of the present invention usually exists as a colorless or pale yellowish solid or viscous liquid at normal temperature and under normal pressure, and can be confirmed by the following means (a) to (c).

(a) Measurement of a proton nuclear magnetic resonance spectrum ($^1$H-NMR) indicates peaks based on an aromatic proton and an alkene proton near δ5.9 to 9.0 ppm and peaks based on protons of an alkyl group and an alkylene group near δ1.0 to 4.0 ppm. Upon relatively comparing the spectrum intensities, further, the numbers of protons in the bonding groups can be known.

(b) The compositions of the corresponding products can be determined by the elemental analysis.

(c) Measurement of a $^{13}$C-nuclear magnetic resonance spectrum ($^{13}$C-NMR) indicates a peak based on a carbon atom of an aromatic hydrocarbon group near δ110 to 160 ppm, peaks based on carbon atoms of an alkene near δ80 to 140 ppm, and peaks based on carbon atoms of an alkyl group and an alkylene group near δ20 to 80 ppm.

[Preparation of Chromene Compound]

There is no particular limitation on the method of preparing a chromene compound represented by the general formula (1) of the present invention, and any synthesizing method may be employed. Described below is a representative method that is generally preferably employed.

A method in which a naphthol derivative represented by the following general formula (6)

wherein R3, R4, R5, R6, R7, R8, R9 and R10 are as defined in the above general formulas (1), (2) and (3), are reacted together in the presence of an acid catalyst.

There is no particular limitation on the method of synthesizing the naphthol derivative represented by the above general formula (6) which can be preferably produced by, for example, the following method.

That is, 1,1-dichloro-2-naphthalenone is synthesized by the reaction of 2-naphthol with chlorine, and is then reacted with a secondary or primary amine corresponding to the substituent R1 of the above general formula (1) in the presence of a base such as triethylamine to synthesize a 1-chloro-2-naphthol derivative, followed by the reaction with a reducing agent such as Raney nickel to thereby favorably synthesize the naphthol derivative. Here, when there is used a 2-naphthol having substituents at the fifth, sixth, seventh and eighth positions of 2-naphthol, there can be synthesized a chromene compound having substituents at the seventh, eighth, ninth and tenth positions of the naphthopyran ring.

Further, the propargyl alcohol derivative represented by the above general formula (7) can be synthesized by reacting a ketone derivative corresponding to the above general formula (7) with a metal acetylene compound such as lithium acetylide.

There is no particular limitation on the reaction conditions in reacting the naphthol derivative represented by the above general formula (6) with the propargyl alcohol represented by the above general formula (7) in the presence of oxygen, but it is desired to employ the following reaction conditions.

That is, the reaction ratio of these two kinds of compounds can be selected over a wide range. Generally, however, it is desired that the reaction ratio is selected over a range of from 1:10 to 10:1 (molar ratio). As the acid catalyst, further, there can be used sulfuric acid, benzenesulfonic acid, p-toluenesulfonic acid or acidic alumina in an amount over a range of, preferably, from 0.1 to 10 parts by weight per 100 parts by weight of the total of the naphthol derivative and the propargyl alcohol. The reaction temperature is preferably from 0 to 200° C., and it is prefer to use a nonprotonic organic solvent, such as N-methylpyrrolidone, dimethylformamide, tetrahydrofuran, benzene or toluene as the solvent.

There is no particular limitation on the method of refining the reaction product. For example, the product is refined by silica gel column and, then, by recrystallization.

The chromene compound represented by the above general formula (1) of the present invention dissolves well in a general organic solvent such as toluene, chloroform or tetrahydrofuran. When the chromene compound represented by the general formula (1) is dissolved in the above solvent, the solution is usually nearly colorless and transparent, quickly develops a color when it is irradiated with sunlight or ultraviolet rays, and quickly returns to the initial colorless state when it is no longer irradiated with light, thus exhibiting a good photochromic action.

The above photochromic action is similarly expressed even in a high molecular solid matrix. Such a high molecular solid matrix may be any one provided the chromene compound represented by the general formula (1) of the invention homogeneously disperses therein. Optically preferred examples are thermoplastic resins such as polymethylacrylate, polyethylacrylate, polymethylmethacrylate, polyethylmethacrylate, polystyrene, polyacrylonitrile, polyvinyl alcohol, polyacrylamide, poly(2-hydroxyethylmethacrylate), polydimethylsiloxane and polycarbonate.

There can be further exemplified (meth)acrylic acid ester compounds having not less than two (meth)acryloyloxy groups, such as ethylene glycol diacrylate, diethylene glycol dimethacrylate, triethylene glycol dimethacrylate, tetraethylene glycol dimethacrylate, nonaethylene glycol dimethacrylate, tetradecaethylene glycol dimethacrylate, ethylene glycol bisglicidylmethacrylate, bisphenol A dimethacrylate, 2,2-bis(4-methacryloyloxyethoxyphenyl)propane, 2,2-bis(3,5-dibromo-4-methacryloyloxyethoxyphenyl)propane and trimethylolpropane trimethacrylate; multi-valent allyl compounds such as diallyl phthalate, diallyl terephthalate, diallyl isophthalate, diallyl tartarate, diallyl epoxysuccinate, diallyl fumarate, diallyl chloroendoate, diallyl hexaphthalate, diallyl carbonate, diallyl diglycol carbonate, and trimethylolpropanetriallyl carbonate; multi-valent thioacrylic acid and multi-valent thiomethacrylic acid ester compounds such as 1,2-bis(methacryloylthio)ethane, bis(2-acryloylthioethyl)ether, and 1,4-bis(methacryloylthiomethyl)benzene; (meth)acrylic acid ester compounds having one or more functional groups other than the (meth)acryloyloxy group, such as glycidyl acrylate, glycidyl methacrylate, β-methylglicidyl methacrylate, bisphenol A-monoglycidylether methacrylate, 4-glycidyloxy methacrylate, 3-(glicidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate and methoxypolyethylene glycol methacrylate; and thermosetting resins obtained by polymerizing radically polymerizable polyfunctional monomers such as divinyl benzene and the like.

There can be further exemplified copolymers of these monomers with unsaturated carboxylic acids such as acrylic acid, methacrylic acid and maleic anhydride; acrylic acid and methacrylic acid ester compounds such as methyl acrylate, methyl methacrylate, benzyl methacrylate, phenyl methacrylate, and 2-hydroxyethyl methacrylate; fumaric acid ester compounds such as diethyl fumarate and diphenyl fumarate; thioacrylic acid and thiomethacrylic acid ester compounds such as methylthio acrylate, benzylthio acrylate and benzylthio methacrylate; or radically polymerizable monofunctional monomers such as vinyl compounds like styrene, chlorostyrene, methyl styrene vinyl naphthalene, α-methylstyrene dimer, and bromostyrene.

There is no particular limitation on the method of dispersing the chromene compound represented by the general formula (1) of the invention in the high molecular solid matrix, and any generally employed method can be used. For example, the above thermoplastic resin and the chromene compound are kneaded together in a molten state and are dispersed in a resin. Or, the chromene compound is dissolved in the polymerizable monomer followed by the addition of a polymerization catalyst so as to be polymerized by heat or light, and is dispersed in the resin. Or, the surfaces of the thermoplastic resin and the thermosetting resin are dyed with the chromene compound so that it disperses in the resin.

The chromene compound of the present invention can be used as a photochromic material over a wide range, such as various memory materials to substitute for the silver salt photosensitive material, copying material, photosensitive material for printing, memory material for cathode-ray tubes, photosensitive material for laser and photosensitive material for holography. Further, the photochromic material using the chromene compound of the present invention can be used as photochromic lens material, optical filter material, display material, actinometer, ornament, etc.

When used as a photochromic lens, for example, a polymer film in which the photochromic material of the invention is homogeneously dispersed is sandwiched in the lens; the surface of the lens is coated with the polymer film and is further coated with a curing material; the chromene compound of the invention is dispersed in the polymerizable monomer and is polymerized in a predetermined manner; the compound is dissolved in, for example, a silicone oil so that the lens surfaces are impregnated with the compound at 150 to 200° C. for 10 to 60 minutes, and the surfaces are further coated with a curable material, to obtain a photochromic lens having a homogeneous dimming property.

[Photochromic Polymerizable Composition]

Among the above photochromic materials, there is used a photochromic polymerizable composition obtained by dispersing the chromene compound of the invention in a polymerizable monomer in producing a photochromic material that comprises a high molecular matrix.

For example, the photochromic polymerizable composition is poured into a predetermined mold and is polymerized by using a polymerization catalyst to obtain a product.

The photochromic polymerizable composition contains a chromene compound of the invention, a polymerizable monomer and, as require, a polymerization initiator.

<Polymerizable Monomer>

As the polymerizable monomer, there can be exemplified those capable of forming a high molecular matrix described above. Among them, a (meth)acrylic acid ester compound is most desired from the standpoint of transparency of the obtained polymer, dimensional stability and workability.

<Polymerization Initiator>

As the polymerization initiator, there is usually used a radical polymerization initiator. Representative examples include diallyl peroxides such as benzoyl peroxide, p-chlorobenzoyl peroxide, decanoyl peroxide, lauroyl peroxide and acetyl peroxide; peroxy esters such as t-butylperoxy-2-ethyl hexanate, t-butylperoxy neodecanate, cumylperoxy neodecanate, t-butylperoxy benzoate, t-butylperoxy isobutylate and 1,1,3,3-tetramethylbutylperoxy-2-ethyl hexanate; percarbonates such as diisopropylperoxy carbonate and di-sec-butylperoxy dicarbonate; and azo compounds such as azobisisobutylonitrile, etc. As the photopolymerization catalyst, there can be exemplified acetophenone compounds such as 1-phenyl-2-hydroxy-2-methylpropane-1-one, 1-hydroxycyclohexylphenylketone, and 1-(4- isopropylphenyl)-2-hydroxy-2-methylpropane-1-one; α-carbonyl compounds such as 1,2-diphenylethanedione and methylphenyl glyoxylate; and acylphosphinoxide compounds such as 2,6-dimethylbenzoyldiphenyl phosphinoxide, 2,4,6-trimethylbenzoyldiphenyl phosphinoxide, 2,6-dichlorobenzoyldiphenyl phosphinoxide, and 2,6-dimethoxybenzoyl diphenylphosphinoxide. These polymerization initiators may be used alone or in a combination of two or more kinds at any ratio depending upon the monomer that is used. It is further allowable to use a heat polymerization catalyst and a photopolymerization catalyst in combination. When the photopolymerization catalyst is used, a known polymerization promotor such as tertiary amine or the like may be used in combination.

The amount of the polymerization initiator varies depending upon the polymerization conditions, kind of the initiator and composition of the polymerizable monomer, and cannot be definitely stated. Generally, however, the polymerization initiator is used in an amount of from 0.001 to 10 parts by weight and, preferably, from 0.01 to 5 parts by weight per 100 parts by weight of the whole polymerizable monomers.

<Other Components>

The photochromic polymerizable composition of the present invention can be blended with a variety of additives depending upon the use of the photochromic material obtained by polymerizing and curing the polymerizable composition in order to improve its properties but in amounts in which they will not impair the effect of the invention.

For example, the chromene compound used in the present invention can be combined with other known photochromic compounds to obtain a photochromic composition. There is no particular limitation on the other photochromic compounds that are to be used in combination, and any known photochromic compound can be used. For example, there can be used, in combination, an oxazine compound, a fulgimide compound and/or a known chromene compound (hereinafter referred to as "other known chromene compound") other than the chromene compound used in the invention.

In the present invention, there is no particular limitation on the mixing ratio of the oxazine compound, fulgimide compound and other known chromene compounds, and the mixing ratio may be suitably determined by taking the properties of the photochromic compounds into consideration. When the oxazine compound, fulgimide compound and/or other known chromene compounds are to be added to the photochromic polymerizable composition of the present invention, the amount of their addition is usually from 0.001 to 10 parts by weight and, preferably, from 0.01 to 1 part by weight per 100 parts by weight of the whole monomers.

An ultraviolet-ray stabilizer may be added to the photochromic polymerizable composition of the present invention. Addition of the ultraviolet-ray stabilizer further lengthens the durability of photochromic property. In particular, use of the fulgimide compound improves the durability. When a neutral tint is developed by using the oxazine compound and the fulgimide compound in combination, therefore, a change does not occur in the color tone of a neutral tint at the time of developing color even after aged.

As the ultraviolet-ray stabilizer, there can be used any known one without limitation, such as hindered amine photostabilizer, hindered phenol photostabilizer, sulfur-type antioxidant and phosphorous acid ester-type photostabilizer.

Though there is no particular limitation on their amount of use, the ultraviolet-ray stabilizers are usually used in an amount of from 0.01 to 5 parts by weight and, preferably, from 0.02 to 1 part by weight per 100 parts by weight of the whole monomers.

As required, further, there can be added various additives such as benzotriazole-type ultraviolet-ray absorbing agent or benzophenone-type ultraviolet-ray absorbing agent, antioxidant, coloring-preventing agent, antistatic agent, fluorescent dye, pigment and perfume.

<Polymerization and Curing of Polymerizable Composition>

Next, described below is a method of obtaining the photochromic material of the present invention by polymerizing and curing the photochromic polymerizable composition of the present invention.

There is no particular limitation on the polymerization method of obtaining a polymer from the photochromic polymerizable composition of the present invention, and any known polymerization method can be employed. The polymerization means is conducted by using various peroxides and a polymerization initiator such as azo compound, or by the irradiation with ultraviolet rays, α-rays, β-rays or γ-rays, or by utilizing both of them. A representative polymerization method may be a cast polymerization by pouring the photochromic polymerizable composition of the invention containing a radical polymerization initiator into a mold supported by elastomer gaskets or spacers, polymerizing the composition in a heating furnace or by the irradiation with ultraviolet rays or visible light and, then, removing the polymer.

Among the polymerization conditions, the polymerization temperature differs depending upon the kind of the polymerizable monomer and the polymerization initiator and cannot be definitely specified. Usually, however, a so-called tapered two-stage polymerization is conducted by starting the polymerization at a relatively low temperature, slowly raising the temperature and curing the composition at a high temperature at the time when the polymerization has finished. The polymerization time, too, varies depending upon various factors like the temperature and it is desired to determine an optimum time in advance depending upon the conditions. Generally, however, it is desired that the polymerization is completed in 2 to 40 hours.

EXAMPLES

The invention will be described in further detail by way of Examples to which only, however, the invention is in no way limited.

Example 1

3.2 Grams (0.014 mols) of the following naphthalene derivative,

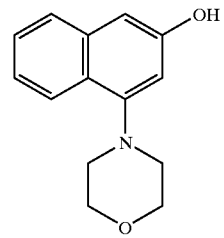

and 5.0 g (0.014 mols) of the following propargyl alcohol derivative,

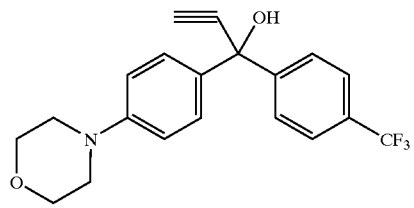

were dissolved in 200 ml of toluene, followed by the addition of 0.05 g of a p-toluenesulfonic acid, and the mixture was refluxed for one hour. After the reaction, the solvent was removed, and the reaction product was refined by chromatography on silica gel by using a mixture solvent of chloroform and ethyl acetate (9:1) as an eluate to obtain 0.2 g of an orange powdery product, yield, 2.5%.

Elemental analysis of the product showed C, 71.43%; H, 5.36%; F, 9.88%; N, 4.79%; O, 8.44%; which were in very good agreement with the calculated values of C, 71.32%; H, 5.46%; F, 9.95%; N, 4.89%; O, 8.38% of $C_{34}H_{31}F_3NO_3$.

A measurement of a proton nuclear magnetic resonance spectrum indicated peaks of 16H based on a methylene proton of morpholino group near δ3.1 to 3.2, δ3.8 to 4.0 ppm, and peaks of 15H based on an aromatic proton and an alkene proton near δ6.0 to 8.1 ppm.

Further, a measurement of a $^{13}C$-nuclear magnetic resonance spectrum indicated a peak based on a carbon atom of an aromatic ring near δ110 to 160 ppm, a peak based on a carbon atom of an alkene near δ80 to 140 ppm, and a peak based on a carbon atom of an alkyl at δ20 to 60 ppm.

From the above results, it was confirmed that the isolated product was a compound represented by the following structural formula (8) that corresponds to the chromene compound 2,

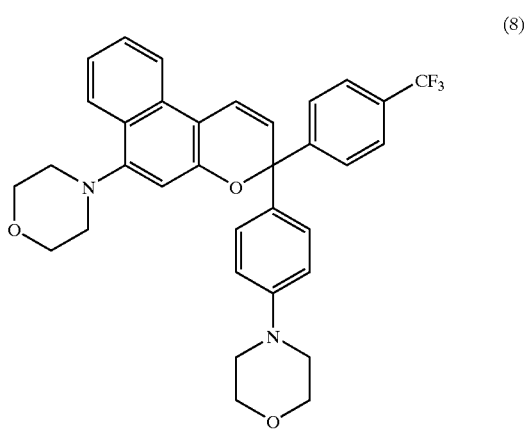

(8)

Examples 2 to 6

Chromene compounds corresponding to the chromene compound 2 shown in Tables 1 and 2 were synthesized in the same manner as in Example 1. The obtained products were analyzed for their structures relying on the same means for confirming structure as that of Example 1. It was confirmed that the obtained products were the compounds represented by the structural formulas shown in Tables 1 and 2. Table 3 shows values of elemental analysis of these compounds, values calculated from the structural formulas of these compounds, and characteristic spectra in $^1H$-NMR spectra.

TABLE 1

| Example | Starting material | |
|---|---|---|
| No. | Naphthol derivative | Propargyl alcohol derivative |
| 2 | | |
| 3 | | |

TABLE 1-continued

| Example No. | | product | Yield (%) |
|---|---|---|---|
| 4 | naphthol-morpholine structure | propargyl alcohol with piperidinyl-phenyl and phenylsulfonyl-phenyl structure | |
| 2 | | fluorophenyl/morpholinophenyl naphthopyran | 11 |
| 3 | | cyanophenyl/morpholinophenyl indoline-naphthopyran | 8 |
| 4 | | phenylsulfonylphenyl/piperidinophenyl morpholino-naphthopyran | 5 |

TABLE 2

| Example No. | Starting material | |
|---|---|---|
| | Naphthol derivative | Propargyl alcohol derivative |
| 5 | (4-morpholino-2-naphthol) | (1-(4-morpholinophenyl)-1-(3,4-bis(trifluoromethyl)phenyl)prop-2-yn-1-ol) |
| 6 | (7-methoxy-4-morpholino-2-naphthol) | (1-(4-carbazolylphenyl)-1-(2-fluoro-4-trifluoromethylphenyl)prop-2-yn-1-ol) |

| Example No. | product | Yield (%) |
|---|---|---|
| 5 | (corresponding naphthopyran product) | 16 |
| 6 | (corresponding naphthopyran product) | 13 |

TABLE 3

| Ex. No. | Found | | | | | Calculated | | | | | 1H-NMR (ppm) |
|---|---|---|---|---|---|---|---|---|---|---|---|
| | C | H | N | O | Others | C | H | N | O | Others | |
| 2 | 75.88 | 6.00 | 5.22 | 9.29 | F3.77 | 75.84 | 5.98 | 5.36 | 9.18 | F3.64 | δ5.6~9.0:15H<br>δ3.0~4.0:16H |
| 3 | 81.29 | 5.67 | 7.37 | 5.67 | | 81.26 | 5.56 | 7.48 | 5.70 | | δ5.6~9.0:19H<br>δ3.0~4.0:10H<br>δ1.5~2.5:2H |
| 4 | 74.96 | 5.79 | 4.31 | 9.99 | S5.01 | 74.74 | 5.96 | 4.36 | 9.96 | S4.99 | δ5.6~9.0:20H<br>δ2.0~4.5:18H |
| 5 | 65.66 | 4.74 | 4.48 | 7.55 | F17.74 | 65.62 | 4.72 | 4.37 | 7.49 | F17.79 | δ5.6~9.0:14H<br>δ3.0~4.5:16H |
| 6 | 73.75 | 4.62 | 3.99 | 6.82 | F11.01 | 73.70 | 4.60 | 4.00 | 6.85 | F10.84 | δ5.6~9.0:23H<br>δ3.0~4.5:11H |

Example 7

0.05 Parts (hereinafter, parts are all by weight) of the chromene compound obtained in Example 1 were added to 70 parts of a tetraethylene glycol dimethacrylate, 15 parts of a triethylene glycol dimethacrylate, 10 parts of a glycidyl methacrylate, 5 parts of a 2-hydroxyethyl methacrylate and 1 part of a perbutyl ND (manufactured by Nihon Yushi Co.) and were mixed sufficiently. The mixture solution was poured into a mold constituted by glass plates and gaskets of an ethylene/vinyl acetate copolymer, and was cast-polymerized. The polymerization was conducted by using an air furnace, gradually elevating the temperature from 30° C. to 90° C. over 18 hours and maintaining the temperature of 90° C. for 2 hours. After the polymerization, the polymer (photochromic polymer) was removed from the glass mold.

The obtained polymer (2 mm thick) was irradiated with light by using a xenon lamp L-2480 (300 W) SHL-100 manufactured by Hamamatsu Photonics Co. through an aeromass filter (manufactured by Coning Co.) at 20±1° C. at beam intensities on the polymer surface of 365 nm=2.4 mW/cm$^2$ and 245 nm=24 µW/cm$^2$ for 120 seconds to develop color and to measure the photochromic properties. The photochromic properties were evaluated in a manner as described below.

① Maximum absorption wavelength (λmax): A maximum absorption wavelength after the development of color as found by using a spectrophotometer (instantaneous multichannel photodetector MCPD 1000) manufactured by Otsuka Denshi Co. The maximum absorption wavelength is related to the color tone at the time when the color is developed.

② Color density {ε(120)–ε(0)}: A difference between an absorbancy {ε(120)} after irradiated with light for 120 seconds at the maximum absorption wavelength and the absorbancy ε(0) at the maximum absorption wavelength of when not irradiated with light. It can be said that the higher this value, the more excellent the photochromic properties are.

③ Fading rate [t½ (min)]: The time until the absorbancy of a sample at the maximum wavelength drops down to one-half the {ε(120)–ε(0)} from when the sample is no longer irradiated with light after it was irradiated with light for 120 seconds. When used being mixed with a blue compound to adjust the color tone to a neutral tint, it can be said that the chromene compound should have a fading rate of about 5 to 10 minutes and, particularly, about 7.5 to 8.5 minutes such that the color fades maintaining a uniform color tone, since the blue compound usually has a fading rate of about 3 minutes. It is further desired that the fading rate is as high as possible when the chromene compound is used alone as well as when the chromene compound is used together with other compounds of which the fading rates do not cast any problem.

④ Color developing rate (min.$^{-1}$): An increase in the density of color developed per a unit time when irradiated with light using a xenon lamp until the density of the developed color reaches its saturation.

⑤ Initial color {ε(0)}; Absorbancy in a state of not being irradiated with light at the maximum absorption wavelength. In an optical material such as spectacle lenses, it can be said that the lower this value, the more excellent the photochromic properties are.

The results were as shown in Table 4.

Examples 8 to 12

Photochromic polymers were obtained in the same manner as in Example 7 but using the compounds obtained in Examples 2 to 6 as chromene compounds, and their properties were evaluated. The results were as shown in Table 4.

TABLE 4

| Ex. No. | Compound No. | λ max (nm) | Initial color ε(0) | Color density ε(120) – ε(0) | Fading rate τ/1/2 (min.) | Developing rate (/min.) |
|---|---|---|---|---|---|---|
| 7 | 1 | 468 | 0.04 | 0.98 | 8.0 | 0.61 |
| 8 | 2 | 450 | 0.04 | 0.89 | 7.8 | 0.55 |
| 9 | 3 | 470 | 0.04 | 0.85 | 7.9 | 0.58 |
| 10 | 4 | 474 | 0.05 | 0.96 | 8.1 | 0.63 |
| 11 | 5 | 464 | 0.05 | 0.88 | 7.8 | 0.58 |
| 12 | 6 | 458 | 0.06 | 1.13 | 8.3 | 0.66 |

Comparative Examples 1 to 3

For the purpose of comparison, photochromic polymers were obtained in the same manner as in Example 7 by using the compounds represented by the following formulas (A), (B) and (C), and their properties were evaluated. The results were as shown in Table 5.

The compound of the formula (A) is a chromene compound disclosed in the above-mentioned WO98/45281, the compound of the formula (B) is a chromene compound disclosed in the above-mentioned Japanese Unexamined Patent Publication (Kokai) No. 298176/1998, and the compound of the formula (C) is a chromene compound disclosed in U.S. Pat. No. 4,980,089.

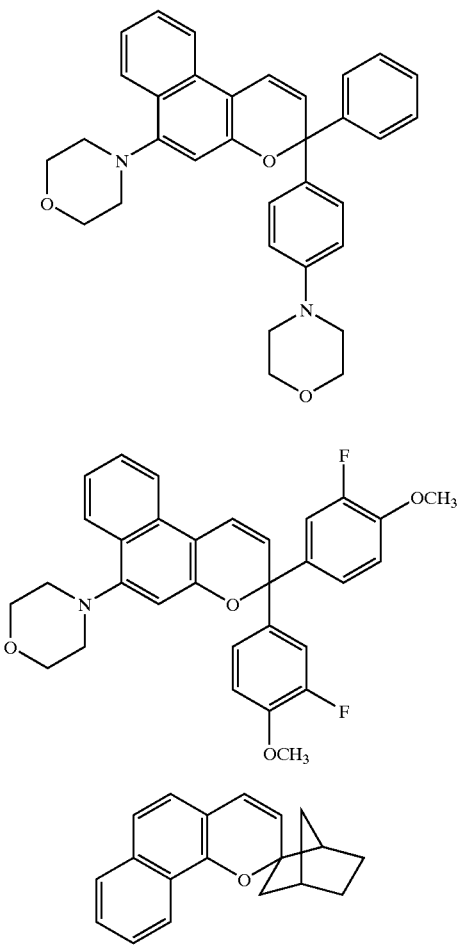

(A)

(B)

(C)

TABLE 5

| Comp. Ex. No. | Compound No. | λ max (nm) | Initial color ε (0) | Color density ε (120) − ε (0) | Fading rate τ/1/2 (/min.) | Developing rate (min.) |
|---|---|---|---|---|---|---|
| 1 | (A) | 478 | 0.15 | 1.00 | 2.6 | 0.62 |
| 2 | (B) | 442 | 0.05 | 1.10 | 4.0 | 0.6 |
| 3 | (C) | 450 | 0.01 | 1.01 | >20 | 0.2 |

The photochromic polymer of Comparative Example 1 has a good color density and a good color-developing rate but has a large degree of initial color. Further, the fading rate is so high that a balance in the color tone is not favorably maintained at the time of fading when the photochromic polymer is used in combination with the blue compound.

The photochromic polymer of Comparative Example 2 exhibits initial color which is improved to a degree which is free from any problem compared with that of Comparative Example 1, and has a slightly decreased fading rate. However, the fading rate is not still satisfactory, and the above-mentioned problem still remains when the photochromic polymer is used in combination with the blue compound.

The photochromic polymer of Comparative Example 3 is free from problem with respect to color density, color-developing rate and initial color, but the color-developing rate and the fading rate are too low that a balance in the color tone is not favorably maintained not only at the time of fading but also at the time of developing color.

In Examples 7 to 12 using the chromene compound 2 of the present invention, on the other hand, the photochromic polymers exhibit large color densities, little initial colors, as well as fading rates which are low to a suitable degree and large color-developing rates (comparable to that of the blue compound). When these photochromic polymers are used in combination with the blue compound, therefore, a balance in the color tone is favorably maintained at the time of developing color and at the time of fading color.

Example 13

1.0 Gram (0.0043 mols) of the following naphthalene derivative,

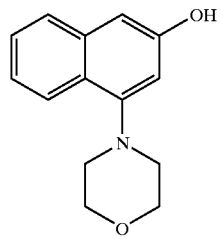

and 1.5 g (0.0047 mols) of the following propargyl alcohol derivative,

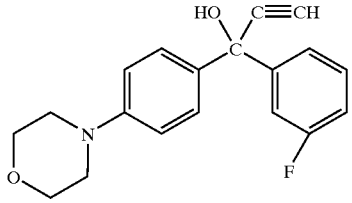

were dissolved in 50 ml of toluene, followed by the addition of 0.05 g of a p-toluenesulfonic acid, and the mixture was refluxed for one hour. After the reaction, the solvent was removed, and the reaction product was refined by chromatography on silica gel to obtain 0.56 g of a pale yellowish powdery product, yield, 25%.

Elemental analysis of the product showed C, 75.80%; H, 6.0%; F, 3.63%; N, 5.33%; O, 9.16%; which were in very good agreement with the calculated values of C, 75.84%; H, 5.98%; F, 3.64%; N, 5.36%; O, 9.18% of $C_{33}H31FN_2O_3$.

Figure 2:
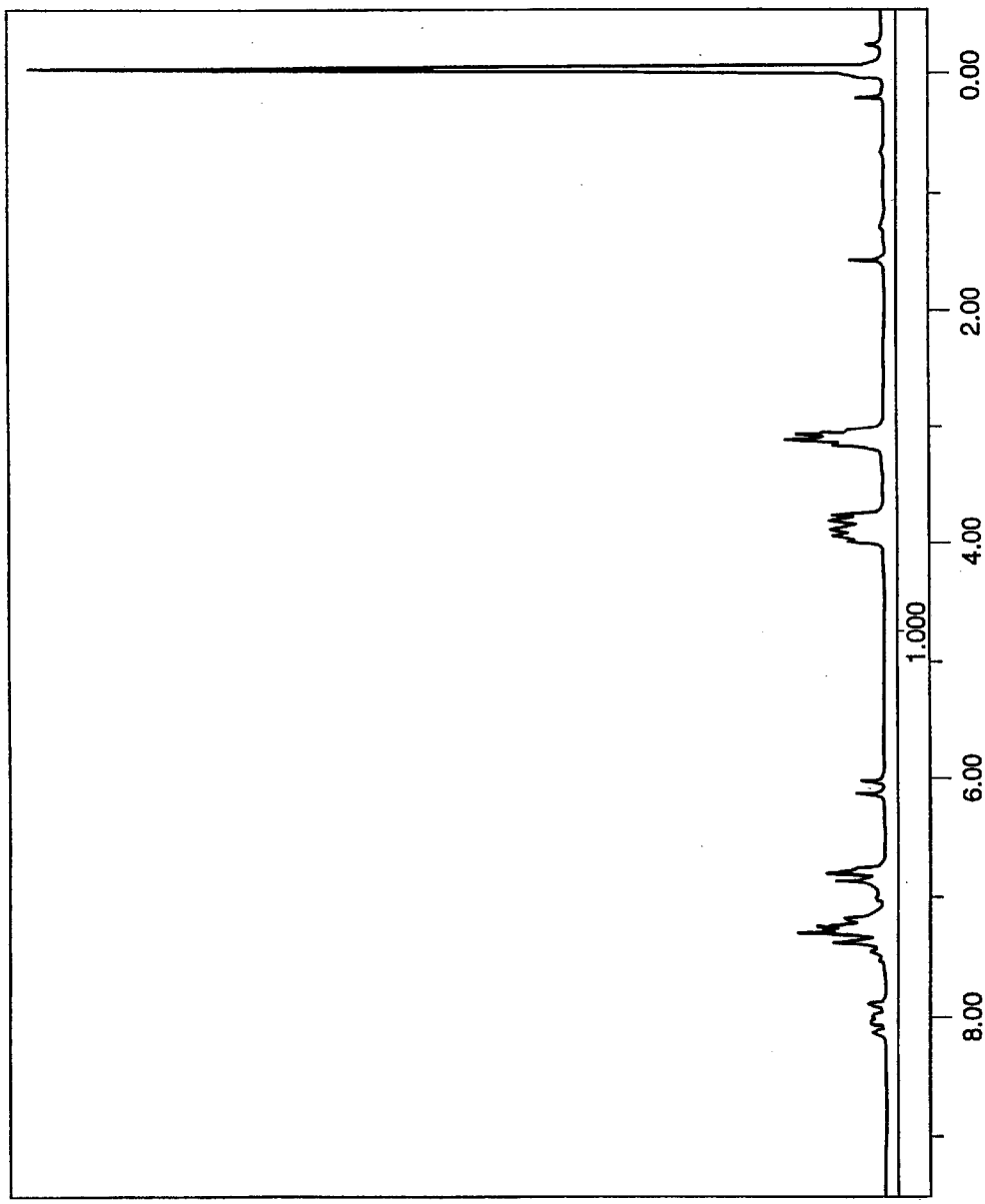
FIG. 2 shows proton nuclear magnetic resonance spectra of a compound of Example 13.

A measurement of a proton nuclear magnetic resonance spectrum indicated, as shown in FIG. 2, peaks of 16H based on a methylene proton of morpholino group near δ3.0 to 3.2, δ3.7 to 3.8 ppm, and peaks of 15H based on an aromatic proton and an alkene proton near δ6.0 to 8.4 ppm.

Further, a measurement of a $^{13}$C-nuclear magnetic resonance spectrum indicated a peak based on a carbon atom of an aromatic ring near δ110 to 160 ppm, a peak based on a carbon atom of an alkene near δ80 to 140 ppm, and a peak based on a carbon atom of an alkyl at δ20 to 60 ppm.

From the above results, it was confirmed that the isolated product was a compound represented by the following structural formula (9) that corresponds to the chromene compound 3, (9)

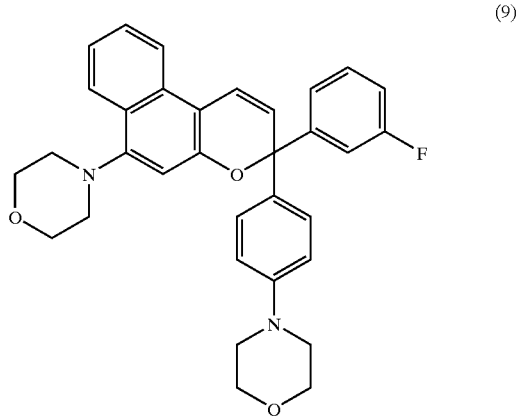

Examples 14 to 21

Chromene compounds corresponding to the chromene compound 3 shown in Table 6 were synthesized in the same manner as in Example 13. The obtained products were analyzed for their structures relying on the same means for confirming structure as that of Example 1. It was confirmed that the obtained products were the compounds represented by the structural formulas shown in Tables 6 and 7. Table 8 shows values of elemental analysis of these compounds, values calculated from the structural formulas of these compounds, and characteristic spectra in $^1$H-NMR spectra.

TABLE 6

| Example No. | Starting material | |
|---|---|---|
| | Naphthol derivative | Propargyl alcohol derivative |
| 14 | | |
| 15 | | |
| 16 | | |
| 17 | | |

TABLE 6-continued

| Example No. | product | Yield (%) |
|---|---|---|
| 14 | | 25 |
| 15 | | 23 |
| 16 | | 22 |
| 17 | | 21 |

TABLE 7

| Example No. | Starting material | |
|---|---|---|
| | Naphthol derivative | Propargyl alcohol derivative |
| 18 | [4-morpholino-3-hydroxynaphthalene structure] | [1-(4-morpholinophenyl)-1-(3-fluoro-4-methoxyphenyl)-2-propyn-1-ol structure] |
| 19 | [4-morpholino-3-hydroxynaphthalene structure] | [1-(4-diphenylaminophenyl)-1-(3-fluorophenyl)-2-propyn-1-ol structure] |
| 20 | [4-morpholino-3-hydroxynaphthalene structure] | [1-(4-carbazolylphenyl)-1-(3-chlorophenyl)-2-propyn-1-ol structure] |
| 21 | [4-morpholino-3-hydroxynaphthalene structure] | [1-(3-dimethylaminophenyl)-1-(4-methoxyphenyl)-2-propyn-1-ol structure] |

| Example No. | product | Yield (%) |
|---|---|---|
| 18 | [chromene product structure with OCH3, F, morpholino, and 4-morpholinophenyl substituents] | 24 |

TABLE 7-continued
| | | |
|---|---|---|
| 19 | 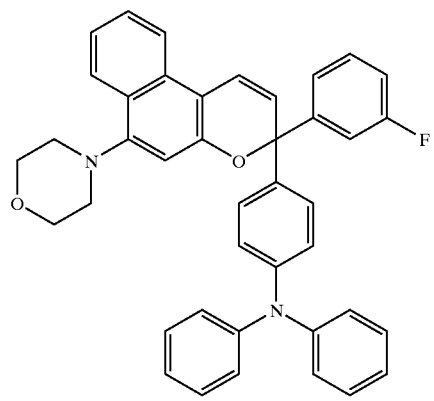 | 19 |
| 20 | 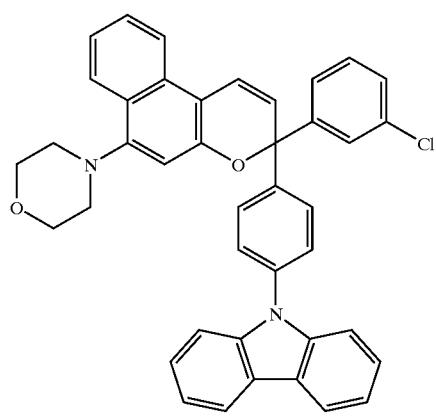 | 12 |
| 21 | 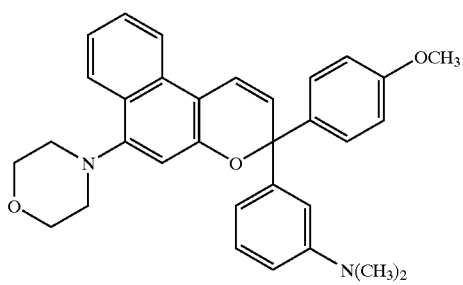 | 15 |
TABLE 8
| Ex. No. | Elemental analysis | | | | | | | | | | 1H-NMR (ppm) |
|---|---|---|---|---|---|---|---|---|---|---|---|
| | Found | | | | | Calculated | | | | | |
| | C | H | N | O | Others | C | H | N | O | Others | |
| 14 | 71.35 | 5.47 | 4.85 | 8.35 | F9.98 | 71.32 | 5.46 | 4.89 | 8.38 | F9.95 | δ5.6~9.0:15H<br>δ3~4.0:16H |
| 15 | 69.42 | 5.33 | 4.75 | 10.88 | F9.62 | 69.38 | 5.31 | 4.76 | 10.87 | F9.68 | δ5.6~9.0:15H<br>δ3.0~4.0:16H |
| 16 | 82.84 | 6.03 | 5.20 | 5.93 | | 82.81 | 6.01 | 5.22 | 5.96 | | δ5.6~9.0:20H<br>δ3.0~4.0:10H<br>δ1.5~2.5:2H |
| 17 | 73.35 | 5.62 | 5.17 | 8.86 | F7.0 | 73.32 | 5.59 | 5.18 | 8.88 | F7.03 | δ5.6~9.0:22H<br>δ3.0~4.5:8H |
| 18 | 73.91 | 6.04 | 5.05 | 11.52 | F3.48 | 73.89 | 6.02 | 5.07 | 11.58 | F3.44 | δ5.6~9.0:14H<br>δ3.0~4.2:19H |
| 19 | 81.44 | 5.52 | 4.61 | 5.26 | F3.16 | 81.43 | 5.50 | 4.63 | 5.29 | F3.14 | δ5.6~9.5:25H<br>δ3.0~4.5:8H |

TABLE 8-continued

| | Elemental analysis | | | | | | | | | 1H-NMR |
|---|---|---|---|---|---|---|---|---|---|---|
| Ex. | Found | | | | | Calculated | | | | |
| No. | C | H | N | O | Others | C | H | N | O | Others | (ppm) |
| 20 | 79.57 | 5.07 | 4.48 | 5.11 | Cl5.77 | 79.53 | 5.05 | 4.52 | 5.17 | Cl5.73 | δ5.6~9.0:25H<br>δ3.0~4.5:8H |
| 21 | 78.07 | 6.57 | 5.68 | 9.71 | | 78.02 | 6.55 | 5.69 | 9.74 | | δ5.6~9.0:15H<br>δ3.0~4.5:17H |

Examples 22 to 30

Photochromic polymers were obtained in the same manner as in Example 7 by using the chromene compounds obtained in Examples 13 to 21. The obtained photochromic polymers were measured for their maximum absorption wavelengths, initial colors, densities of the developed colors and color fading rates in the same manner as in Example 7. The results were as shown in Table 9.

TABLE 9

| Ex. No. | Compound No. | λ max (nm) | Initial color ε (0) | Color density ε (120) – ε (0) | Fading rate τ/1/2 (min.) |
|---|---|---|---|---|---|
| 22 | 13 | 472 | 0.04 | 1.00 | 2.6 |
| 23 | 14 | 468 | 0.03 | 1.10 | 2.8 |
| 24 | 15 | 468 | 0.04 | 0.95 | 2.4 |
| 25 | 16 | 460 | 0.06 | 0.80 | 2.0 |
| 26 | 17 | 466 | 0.03 | 0.90 | 2.8 |
| 27 | 18 | 478 | 0.05 | 1.00 | 2.5 |
| 28 | 19 | 470 | 0.04 | 0.92 | 2.9 |
| 29 | 20 | 470 | 0.05 | 1.00 | 2.3 |
| 30 | 21 | 458 | 0.06 | 0.90 | 2.0 |

As shown in FIG. 9, the photochromic polymers of Examples 22 to 30 using the chromene compound 3 exhibited high densities of the developed colors, little initial colors, large fading rates, and are superior to the photochromic polymer of Comparative Example 1 on account of their small degrees of initial colors, and are superior to the photochromic polymers of Comparative Examples 2 and 3 on account of their large fading rates.

The chromene compounds of the present invention have such features as high densities of the developed colors and small degrees of initial colors.

Depending upon the combinations of the substituents, further, it is allowed to obtain (1) such additional effects as a nearly equal color-developing rate to that of the blue compound that is now being used and a color fading rate which is small to a suitable degree, or (2) such an additional effect that the color fading rate is large. When the chromene compound 2 of the invention that exhibits the former additional effects is used for the photochromic spectacle lenses in combination with the blue compound so as to exhibit a neutral tint at the time of developing the color, color can be faded uniformly without losing balance in the color tone at the time when the color fades. The chromene compound 3 of the invention that exhibits the latter additional effect exhibits, by itself, excellent photochromic properties. Therefore, the excellent photochromic properties are exhibited when the chromene compound 3 of the invention is used alone as well as when the chromene compound 3 of the invention is used in combination with other photochromic compounds having excellent photochromic properties.

What is claimed is:

1. A chromene compound represented by the following formula (1),

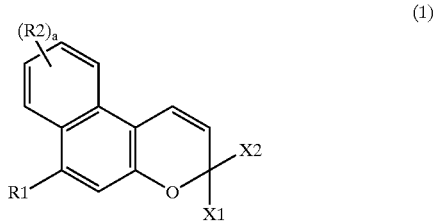

(1)

wherein

R1 is (1) a substituted amino group, (2) a substituted or unsubstituted heterocyclic group having a nitrogen atom, as a hetero atom, wherein said hetero atom is bonded to the naphthopyran ring via the nitrogen atom or (3) a condensed heterocyclic group in which said heterocyclic group is condensed with an aromatic hydrocarbon ring or an aromatic heterocyclic ring, R2 is an alkyl group, an alkoxyl group, an aralkoxyl group, an aralkyl group, a substituted amino group, a cyano group, a substituted or unsubstituted aryl group, a halogen atom, a substituted or unsubstituted heterocyclic group having, as a hetero atom, a nitrogen atom, wherein said hetero atom is bonded to the naphthopyran ring via the nitrogen atom, or a condensed heterocyclic group in which said heterocyclic group is condensed with an aromatic hydrocarbon ring or an aromatic heterocyclic ring, "a" is an integer of 0 to 3, X1 is a group represented by the following formula (2),

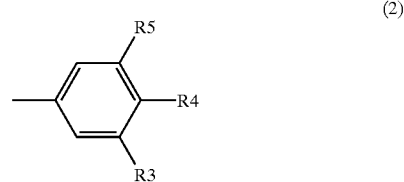

(2)

wherein each of R3, R4 and R5 is a hydrogen atom, a substituted amino group, a substituted or unsubstituted heterocyclic group having a nitrogen atom, as a hetero atom, bonded to the benzene ring via said nitrogen atom, or a condensed heterocyclic group in which said heterocyclic group is condensed with an aromatic hydrocarbon ring or an aromatic heterocyclic ring, provided that R3, R4 and R5 are not hydrogen atoms simultaneously, and X2 is a group represented by the following formula (3),

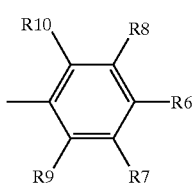

(3)

wherein

R6 is a hydrogen atom; an electron attractive group selected from the group consisting of a trifluoromethyl group, a trifluoromethoxy group, a cyano group, a sulfonyl group, an alkylsulfonyl group, an arylsulfonyl group and a nitro group; or an alkoxyl group, each of R7 and R8 is (i) a hydrogen atom, an aliphatic hydrocarbon group having more than three carbon atoms, a halogen atom, a trifluoromethyl group, a trifluoromethoxy group, a cyano group, a sulfonyl group, an alkylsulfonyl group, an arylsulfonyl group or a nitro group when R6 is not a hydrogen atom, or (ii) a hydrogen atom, a halogen atom, a trifluoromethyl group or a trifluoromethoxy group when R6 is a hydrogen atom, each of R9 and R10 is a hydrogen atom a cyano group, an alkoxyl group having 1 to 5 carbon atoms, a fluorine atom or a chlorine atom, provided that (1) when R4 in the group represented by the above formula (2) is a substituted amino group, a substituted or unsubstituted heterocyclic group or is a condensed heterocyclic group, R6 is not an alkoxyl group, and R6, R7, R8, R9 and R10 are not hydrogen atoms simultaneously
and (2) when R1 is a substituted or unsubstituted heterocyclic group having a nitrogen atom, as a hetero atom, wherein said hetero atom is bonded to the naphthopyran ring via the nitrogen atom, and "a" is an integer of zero, and X1 is

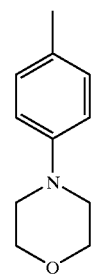

then

X2 is not trifluoromethyl-phenyl.

2. A chromene compound according to claim 1, wherein the group represented by the formula (3) in formula (1):

R6, R7, R8, R9 and R10 are not hydrogen atoms simultaneously,

R6 is a hydrogen atom or an electron attractive group selected from the group consisting of a trifluoromethyl group, a cyano group, a sulfonyl group, an alkylsulfonyl group, an arylsulfonyl group and a nitro group, when R6 is not a hydrogen atom, each of R7 and R8 is a hydrogen atom, an aliphatic hydrocarbon group having more than 3 carbon atoms, a fluorine atom, a trifluoromethyl group, a cyano group, a sulfonyl group, a alkylsulfonyl group, an alkylsulfonyl group, an arylsulfonyl group or a nitro group, and when R6 is a hydrogen atoms, each of R7 and R8 is hydrogen atom.

3. A chromene compound according to claim 1 wherein in the group represented by the formula (3) in formula (1):

R6 is a hydrogen atom, an alkoxyl group or a trifluoromethoxy group, each of R7 and R8 is a hydrogen atom, a halogen atom, a trifluoromethyl group or a trifluoromethoxy group, wherein both R7 and R8 are not hydrogen atoms, when R4 in formula (2) in formula (1) is the substituted amino group the substituted or unsubstituted heterocyclic group, or the condensed heterocyclic group, and both R9 and R10 are hydrogen atoms.

* * * * *